(12) United States Patent
Kinrot et al.

(10) Patent No.: US 9,345,411 B2
(45) Date of Patent: May 24, 2016

(54) DEVICES AND METHODS FOR MONITORING CEREBRAL HEMODYNAMIC CONDITIONS

(75) Inventors: Opher Kinrot, Raanana (IL); Michal Radai, Raanana (IL); Shlomi Ben-Ari, Benyamina (IL)

(73) Assignee: Orsan Medical Technologies, Ltd., Natania (IL)

( * ) Notice: Subject to any disclaimer, the term of this patent is extended or adjusted under 35 U.S.C. 154(b) by 17 days.

(21) Appl. No.: 13/252,186

(22) Filed: Oct. 3, 2011

(65) Prior Publication Data

US 2012/0203091 A1 Aug. 9, 2012

Related U.S. Application Data

(60) Provisional application No. 61/441,248, filed on Feb. 9, 2011, provisional application No. 61/474,739, filed on Apr. 12, 2011.

(51) Int. Cl.
| | | |
|---|---|---|
| *A61B 5/04* | (2006.01) | |
| *A61B 5/00* | (2006.01) | |
| *A61B 5/0265* | (2006.01) | |
| *A61B 5/0295* | (2006.01) | |
| *A61B 5/053* | (2006.01) | |
| *A61B 5/02* | (2006.01) | |
| *A61B 5/05* | (2006.01) | |

(52) U.S. Cl.
CPC ............ *A61B 5/0265* (2013.01); *A61B 5/0295* (2013.01); *A61B 5/053* (2013.01); *A61B 5/4064* (2013.01); *A61B 5/6803* (2013.01)

(58) Field of Classification Search
CPC ............... A61B 5/0476; A61B 5/6814; A61B 5/04012; A61B 5/165; A61B 5/6831; A61B 5/6803; A61B 5/0408; A61B 5/7282; A61B 5/6804; A61B 5/4041; A61B 5/6868
USPC .................. 600/300, 372, 382–383, 386, 388, 600/390–393, 483, 504, 506, 544–545, 547
See application file for complete search history.

(56) References Cited

U.S. PATENT DOCUMENTS

| | | | |
|---|---|---|---|
| 6,214,019 B1 * | 4/2001 | Manwaring et al. | 606/130 |
| 2004/0030258 A1 * | 2/2004 | Williams et al. | 600/544 |
| 2005/0054939 A1 * | 3/2005 | Ben-Ari et al. | 600/506 |
| 2007/0225585 A1 * | 9/2007 | Washbon | A61B 5/0478 600/393 |
| 2009/0088619 A1 * | 4/2009 | Turner | A61B 5/0478 600/383 |

FOREIGN PATENT DOCUMENTS

| | | | | |
|---|---|---|---|---|
| WO | WO2010041204 A1 * | 4/2010 | | |
| WO | WO 2010129026 A2 * | 11/2010 | ........... | A61B 5/0476 |

* cited by examiner

*Primary Examiner* — Joseph Stoklosa
*Assistant Examiner* — Brian M Antiskay
(74) *Attorney, Agent, or Firm* — Finnegan, Henderson, Farabow, Garrett & Dunner, LLP (57) ABSTRACT

Devices, and methods for measuring bioimpedance signals are disclosed. One aspect may include a headset apparatus including a retainer and electrodes. The retainer may be configured to position the electrodes on the head of a subject so as to obtain bioimpedance signals indicative of hemodynamic conditions associated with an MCA territory. A processor may be included to measure and analyze the obtained bioimpedance signals, and to output information for predicting hemodynamic conditions associated with an MCA territory.

22 Claims, 8 Drawing Sheets

DEVICES AND METHODS FOR MONITORING CEREBRAL HEMODYNAMIC CONDITIONS

RELATED APPLICATION

This application claims the benefit of priority under 35 U.S.C. §119(e) of U.S. Provisional Application No. 61/441,248, filed Feb. 9, 2011, and U.S. Provisional Application No. 61/474,739, filed Apr. 12, 2011, both of which are incorporated herein by reference in their entirety.

TECHNICAL FIELD

Aspects of the present disclosure relate to measurement, monitoring and/or analysis of cranial bioimpedance signals, and the prediction of hemodynamic brain conditions based on such analysis.

BACKGROUND

A number of cerebro-hemodynamic parameters may be clinically useful for diagnosing strokes, trauma, and other conditions that can affect the functioning of the cerebrovascular system. These parameters may include cerebral blood volume, cerebral blood flow, cerebral perfusion pressure, mean transit time, time to peak, intracranial pressure, and others. Conventional methods for detecting or monitoring these parameters may include physically inserting a probe into the cerebrospinal fluid or into an artery, angiography, computed tomography angiography (CTA), perfusion computed tomography (PCT), transcranial doppler ultrasound (TCD), positron emission tomography (PET), magnetic resonance imaging (MRI), and angiography (MRA).

Some non-invasive methods for detecting or monitoring cerebro-hemodynamic parameters may require, for example, machines for carrying out CT, PCT, PET, and/or MRI procedures. In some instances, the cost of these machines, their limited mobility, and/or their significant expense per use, may limit their usefulness in situations where either regular, continuous, or frequent monitoring of cerebro-hemodynamic conditions may be desirable.

The foregoing description is merely exemplary for providing general background and is not restrictive of the various embodiments of systems, methods, devices, and features as described and claimed.

SUMMARY OF A FEW ASPECTS OF THE DISCLOSURE

In the presently disclosed embodiments, several exemplary systems and methods are described that may be used to measure and monitor hemodynamic conditions. In some embodiments, these methods and systems may be useful, for example, for continuous or frequent use and may involve, for example, a patient headset apparatus and cerebral perfusion monitor for measuring bioimpedance signals indicative of cerebrovascular hemodynamic conditions. The patient headset and cerebral perfusion monitor may provide information for predicting hemodynamic conditions.

One exemplary disclosed embodiment may include a headset apparatus. The headset apparatus may include a retainer, a first electrode connected to the retainer at a first position such that when the retainer is oriented on a head of a subject, the first electrode is located anterior to the Middle Cerebral Artery (MCA) of a subject and generally opposes an anterior horn of a lateral cerebral ventricle. The headset may also include a second electrode connected to the retainer at a second position, such that when the retainer is oriented on the head of the subject, the second electrode is located posterior to the MCA and generally opposes a posterior horn of the lateral cerebral ventricle. At least one electrical conductor may be associated with the headset to enable the first electrode and the second electrode to be connected in a circuit, such that when the first electrode is in the first position and the second electrode is in the second position and the first and second electrodes are connected to a circuit through which current flows, the retainer, the first electrode, and the second electrode cooperate to enable current to flow from one of the first and second electrodes on one side of the MCA through the lateral cerebral ventricle and to another of the first and second electrodes on a second side of the MCA, opposite the first side.

In other embodiments, the retainer may maintain a spacing of between 70 mm and 100 mm, or between 75 and 95 mm between the first electrode and the second electrode.

In another embodiment, the retainer may position the first and second electrodes according to a sensitivity map.

In still another embodiment, the retainer may position the first electrode to be glued to exposed skin on the forehead and may position the second electrode to be glued to exposed skin above the ear.

In yet another embodiment, the retainer may position the first and second electrodes such that the first and second electrodes are not directly above external blood vessels or muscled areas.

In a further embodiment, the electrodes may be oriented to enable current to pass from the first electrode, through a lateral cerebral ventricle and to the second electrode.

In still another embodiment, the headset apparatus may further comprise a third electrode connected to the retainer at a third position and a fourth electrode connected to the retainer at a fourth position, such that when the retainer is oriented on the head of the subject, the third electrode is located on a side of the head opposite to the first electrode, and the fourth electrode located on a side of the head opposite the second electrode, and wherein the third and fourth electrodes are paired such that current associated with the first and second electrodes is enabled to flow through a first lateral cerebral ventricle, and current associated with the third and fourth electrodes is enabled to flow through a second lateral cerebral ventricle, opposite the first lateral cerebral ventricle.

In other embodiments, at least one processor may be configured to measure at least one bioimpedance signal from the current that flows from one of the first and second electrodes to another of the first and second electrodes, and may be further configured to measure at least one other bioimpedance signal from the current associated with the third and fourth electrodes.

In additional embodiments, the at least one processor may be configured to output information for predicting a hemodynamic condition associated with an MCA territory on a side of the head of the subject on which the first and second electrode are positioned based on the at least one bioimpedance signal, and may be further configured to output information for predicting a hemodynamic condition associated with an MCA territory on a side of the head of the subject on which the third and fourth electrode are positioned based on the at least one other bioimpedance signal.

In still another embodiment, the first and second electrodes may be configured to drive current therebetween and to enable measurement of a resulting voltage.

In a further embodiment, the first electrode may be a first current electrode and the second electrode may be a second current electrode, and the headset apparatus may further include a first voltage electrode and a second voltage electrode, wherein the first and second voltage electrodes are respectively located on the retainer at positions adjacent to the first and second current electrodes.

The foregoing summary and following description of drawings and following detailed description are exemplary of a just a few aspects of the disclosure, are explanatory only, and are not restrictive of the invention, as claimed.

BRIEF DESCRIPTION OF THE DRAWINGS

The accompanying drawings, which are incorporated in and constitute a part of this specification, together with the description, serve to explain the principles of the embodiments described herein.

DETAILED DESCRIPTION

Reference will now be made in detail to exemplary embodiments, with reference to the accompanying drawings. Wherever possible, the same reference numbers will be used throughout the drawings and the following description to refer to the same or like parts. These embodiments are described in sufficient detail to enable those skilled in the art to practice the invention and it is to be understood that other embodiments may be utilized and that changes may be made without departing from the scope of the present invention. The following detailed description, therefore, is not to be interpreted in a limiting sense.

Unless otherwise defined, all technical and/or scientific terms used herein have the same meaning as commonly understood by one of ordinary skill in the art to which the embodiments of the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not necessarily intended to be limiting.

Exemplary disclosed embodiments may include devices and methods for the measurement and monitoring of bioimpedance signals. More specifically, they may include apparatuses for measuring, correlating, and analyzing signals and outputting information for the prediction a hemodynamic brain condition.

Embodiments consistent with the present disclosure may include a headset apparatus. A headset apparatus may include (but does not necessarily include), for example, support elements such as a retainer, headband, or other framework elements to carry or house additional functional elements. Further structures that may be incorporated may include one or more of: electrodes, circuitry, processors, sensors, wires, transmitters, receivers, and other devices suitable for obtaining, processing, transmitting, receiving, and analyzing electrical signals. A headset apparatus may additionally include fasteners, adhesives, and other elements to facilitate attachment to a subject's body. As used herein, a headset apparatus need not include all such features.

Figure 1:
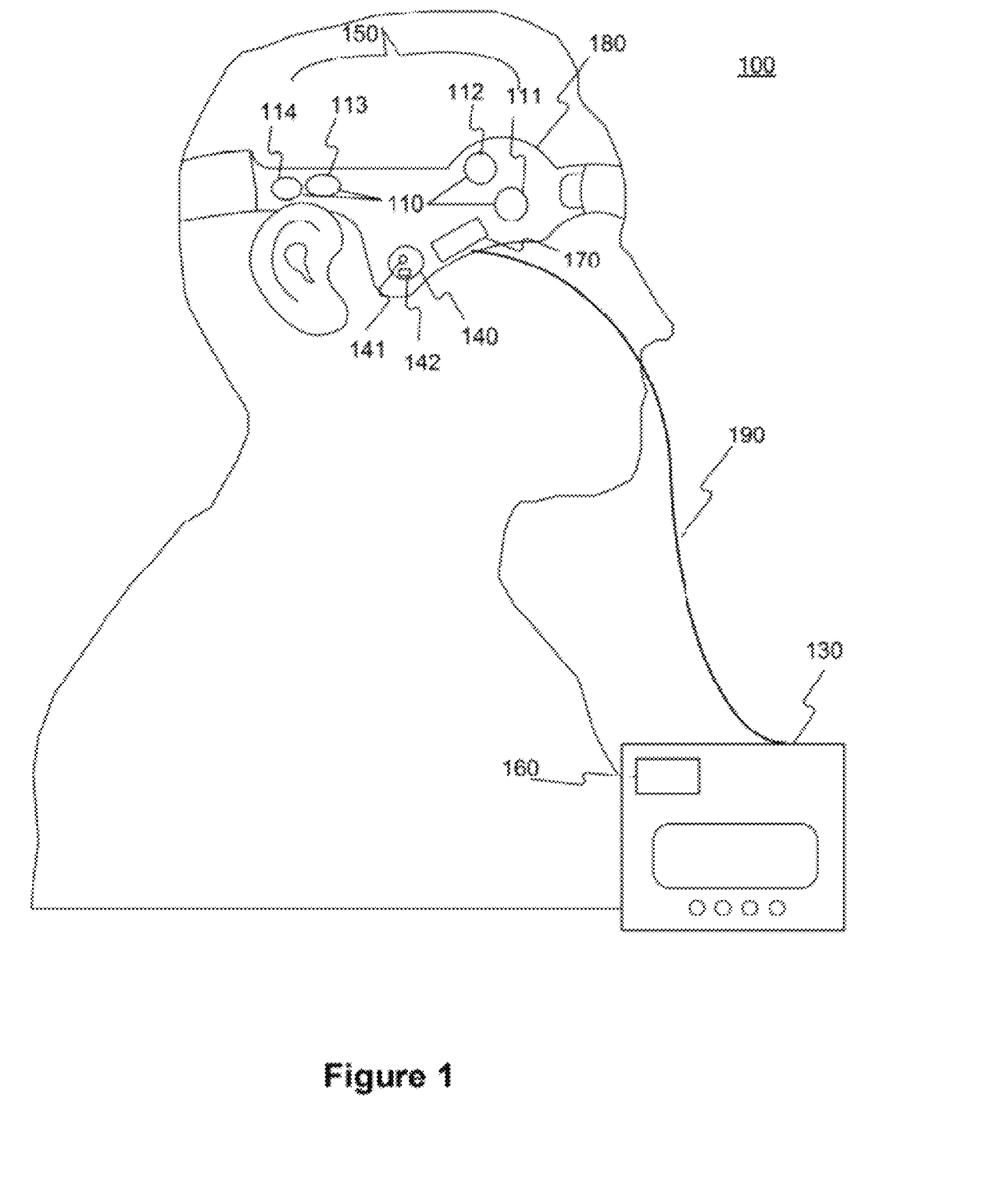
FIG. 1 provides a diagrammatic representation of an exemplary cerebro-hemodynamic measurement apparatus consistent with exemplary embodiments of the invention.

FIG. 1 provides a diagrammatic representation of an exemplary headset apparatus 100. This exemplary apparatus 100 may include electrodes 110 affixed to a subject's head via a retainer 180. Electrodes 110 may be connected to cerebral perfusion monitor 130 via wires (or may alternatively include a wireless connection).

Retainer 180, as illustrated in FIG. 1, may be a headband device. Exemplary retainer 180 may include various means for connecting, encompassing, and affixing electrodes 110 to a patient's head. For example, retainer 180 may include two or more separate sections that are connected to form a loop or a band that circumscribes the patient's head. Any of these aspects, including bands, fasteners, electrode holders, wiring, hook-and-loop connector strips, buckles, buttons, clasps, etc. may be adjustable in order to fit a patient's head. Portions of exemplary retainer 180 may be substantially flexible and portions of the exemplary retainer 180 may be substantially inflexible. For example, electrode-including portions of exemplary retainer 180 may be substantially inflexible in order to, among other things, substantially fix electrodes 110 in specific anatomical positions on the patient's head. In addition to or in the alternative, other portions, such as bands or connectors holding the exemplary retainer 180 to a patient's head, may be substantially flexible, elastic and/or form fitting.

Any portion of exemplary retainer 180 may be specifically designed, shaped or crafted to fit a specific or particular portion of the patient's anatomy. For example, portions of exemplary retainer 180 may be crafted to fit near, around or adjacent to the patient's ear. Portions of exemplary retainer 180 may be specifically designed, shaped or crafted to fit the temples, forehead and/or to position electrodes 110 in specific anatomical or other positions. Portions of the exemplary retainer 180 may be shaped such that electrodes 110 (or other included measurement devices) occur in specific positions for detecting characteristics of blood flow in the head or brain of the patient. Examples of such blood flow may occur in any of the blood vessels discussed herein, especially the arteries and vasculature providing blood to the head and/or brain, regardless of whether the vessels are in the brain or feed the brain.

Exemplary retainer 180 may include features suitable for improving comfort of the patient and/or adherence to the patient. For example, exemplary retainer 180 may include holes in the device that allow ventilation for the patient's skin. Exemplary retainer 180 may further include padding, cushions, stabilizers, fur, foam felt, or any other material for increasing patient comfort.

According to some embodiments of the invention, headset apparatus 100 may include first and second electrodes, connected to a retainer, and at least one electrical conductor to enable a first electrode and a second electrode to be connected in a circuit, such that the retainer, the first electrode, and the second electrode cooperate to enable current to flow from one of the first and second electrodes, through the head of a subject, and to another of the first and second electrodes. As used herein, electrodes may include any device suited to obtain an electrical signal from the head of a subject or deliver an electrical signal to the head of a subject. Electrodes may be constructed of metal or any other conductive or semi-conductive material. In some embodiments, electrodes may contact the skin surface. Skin surface contacting electrodes may be made from a combination of Silver/Silver Halide (Ag/AgCl) in conjunction with solid gel, wet gel, or other conductive gel, as used, for example in ElectroCardiogramGram (ECG) electrodes. Skin preparation methods, such as rubbing, cleansing, or other methods known in the art, may be used to improve skin contact. In other embodiments, electrodes may obtain or deliver an electrical signal without contacting the skin surface.

An electrical conductor to enable first and second electrodes to be connected in a circuit may be any structure capable of conducting a current. For instance, an electrical conductor may include electrical wires of any material connected to the electrodes and/or circuitry printed on flexible or non-flexible substrates. An electrical conductor may be configured to connect first and second electrodes to additional equipment or circuitry configured to generate a current and/or a voltage. Electrical conductors consistent with the present disclosure may also be embedded within a retainer, and/or attached to the surface of a retainer.

In some exemplary embodiments, as illustrated in FIG. 1, first and second electrodes may each be part of a pair of electrodes 110, wherein the pair of electrodes 110 includes a current output electrode and a voltage input electrode. For instance, a first electrode may be a front current electrode 111, and be paired with a front voltage electrode 112. A second electrode may be a rear current electrode 114, and be paired with a rear voltage electrode 113. Front current electrode 111 and rear current electrode 114 may be located at positions adjacent to front voltage electrode 112 and rear voltage electrode 113, respectively. Some embodiments disclosed herein include methods and devices for positioning or locating first and second electrodes. Although the disclosure may refer to first and second electrodes, it is understood that positioning or locating a first or second electrode, for example front current electrode 111, may also include positioning or locating a paired electrode, for example front voltage electrode 112, adjacent to the first or second electrode. Electrodes 110 may also take different shapes, such as circular, elliptical, or other anatomy-conforming shapes. Pairs of electrodes 110 may be adjacent to each other, and may also be arranged as inner and outer electrodes in a concentric pair, having circular or elliptic shape.

Electrodes 111, 112, 113, and 114 may be connected to cerebral perfusion monitor 130 via electrical conductor 190, portions of which may be embedded in retainer 180. Electrical conductor 190, which may include multiple wires, may enable an output current generated by cerebral perfusion monitor 130 to be driven between front current electrode 111 and rear current electrode 114. The output current may include an alternating current (AC) signal of constant amplitude and stable frequency. A resulting voltage induced on the head due to the output current may be measured between front voltage electrode 112 and rear voltage electrode 113. A resulting voltage may be measured at the same frequency as the output current. A comparison between the output current signal and the resultant voltage signal may yield information related to the bioimpedance of the subject. More specifically, an amplitude of the bioimpedance may be computed as a ratio of the resultant voltage signal amplitude to the output current amplitude signal, and a phase of the bioimpedance may be computed as the phase difference by which the output current signal leads the input voltage signal.

The electrodes on exemplary retainer 180 may be arranged so as to obtain bioimpedance signal waveforms. Bioimpedance may be measured by two sensor sections 150, disposed on the right and left sides of the head to correspond with the right and left hemispheres of the brain, for example. While only one sensor section 150 is shown in FIG. 1, an opposite side of the subject's head might include a similar electrode arrangement, including a third and fourth electrode, each including current and voltage electrodes. Each sensor section 150 may include one pair of front electrodes, front current electrode 111 and front voltage electrode 112, and one pair of rear electrodes, rear current electrode 114, and rear voltage electrode 113. The position of the first and second electrodes may be adjusted such that a particular aspect of a cerebro-hemodynamic condition is measured, as will be discussed later in greater detail. The electrode configuration depicted in FIG. 1 is only one example of a suitable electrode configuration. Additional embodiments may include more or fewer electrodes 110, additionally or alternatively arranged in different areas of exemplary retainer 180. Other embodiments may include electrodes 110 configured on an alternatively shaped headset to reach different areas of the subject's head then the exemplary retainer 180. Sections 150 may be separate sections and may be combined in a single retainer 180.

In accordance with some embodiments of the present disclosure, retainer 180 may be configured to position the first electrode to be affixed to exposed skin on the forehead and position the second electrode to be affixed to exposed skin above the ear. Affixing the electrodes to skin with glue may decrease motion artifacts in obtained bioimpedance signals when compared to similar signals obtained from electrodes placed on the hair of a subject. As used herein, the term "glue" is generically used to refer to all types of adhesives, whether applied in a fluid form or whether incorporated in the form of a tacky surface such as with an adhesive sticker. Areas on the forehead, such as just below the hairline, and areas above and around the ears, such as behind the earlobes, may provide exposed skin for affixing of electrodes. Motion artifacts due to electrode placement on the hair of a subject may also be addressed through processing methods. Retainer 180 may also be configured to position first and second electrodes such that the first and second electrodes are not directly above external blood vessels or muscled areas. Such external blood vessels and muscled areas may produce bioimpedance signal artifacts that do not indicate changes in cerebro-hemodynamic conditions. Locations high on the forehead, just below the hairline, so as to avoid muscles around the eyes, and locations above the ears, so as to avoid external blood vessels in front of and behind the ears may be suitable for this embodiment. Signal artifacts caused by external blood vessels or muscled areas may also be addressed through processing methods.

In some exemplary embodiments consistent with the disclosure, a headset apparatus may include at least one processor configured to perform an action. As used herein, the term "processor" may include an electric circuit that performs a logic operation on an input or inputs. For example, such a processor may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations. The at least one processor may be configured to perform an action if it is provided with access to, is programmed with, includes, or is otherwise made capable carrying out instructions for performing the action. The at least one processor may be provided with such instructions either directly through information permanently or temporarily maintained in the processor, or through instructions accessed by or provided to the processor. Instructions provided to the processor may be provided in the form of a computer program comprising instructions tangibly embodied on an information carrier, e.g., in a machine-readable storage device, or any tangible computer-readable medium. A computer program may be written in any form of programming language, including compiled or interpreted languages, and it can be deployed in any form, including as a standalone program or as one or more modules, components, subroutines, or other unit suitable for use in a computing environment. The at least one processor may include specialized hardware, general hardware, or a combination of both to execute related instructions. The processor may also include an integrated communications interface, or a communications interface may be included separate and apart from the processor. The at least one processor may be configured to perform a specified function through a connection to a memory location or storage device in which instructions to perform that function are stored.

In some embodiments, a processor may be configured to receive a signal. As used herein, a signal may be any time-varying or spatially-varying quantity. Receiving a signal may include obtaining a signal through conductive means, such as wires or circuitry; reception of a wirelessly transmitted signal; and/or reception of a signal previously recorded, such as a signal stored in memory. Receiving a signal may further encompass other methods known in the art for signal reception.

Consistent with some embodiments of the present disclosure, the at least one processor may be configured to measure at least one bioimpedance signal from the current that flows from one of the first and second electrodes to another of the first and second electrodes. A bioimpedance signal may include at least one voltage signal, and/or at least one current signal. For example, a bioimpedance signal may include two or more voltage and/or current signals, and may include a signal representative of a comparison between two or more voltage and/or current signals. A bioimpedance signal may be measured as a response to at least one measurement voltage signal, and/or at least one measurement current signal. In a bioimpedance signal, information about the electrical impedance of a subject's body may be contained in the amplitude, frequency, or phase angle of the signal. Information about the electrical impedance of a subject's body may also be contained in a comparison between the amplitudes, frequencies, or phase angles of multiple signals.

In some embodiments, measuring a bioimpedance signal from a current that flows between first and second electrodes may include measuring a resulting voltage at locations adjacent to the first and second electrodes. In alternative or additional embodiments, measuring a bioimpedance signal from a current that flows between first and second electrodes may include the use of a known impedance in the circuit with the electrodes. Further embodiments may include measuring a bioimpedance signal from a current that flows between first and second electrodes using any method known to those skilled in the art.

A current driven between front current electrode 111 and rear current electrode 114 requires a certain driving voltage. The required driving voltage may depend on the impedance of the pathway the current follows between front current electrode 111 and rear current electrode 114. Cerebral perfusion monitor 130 may be configured to drive a certain amount of current, and to measure the resulting voltage required to drive that current. As previously noted, an amplitude of a bioimpedance signal may be computed as a ratio of the resulting voltage signal amplitude to the output current amplitude signal, and a phase of the bioimpedance may be computed as the phase difference by which the output current signal leads the input voltage signal. In one alternative embodiment, cerebral perfusion monitor 130 may be configured to maintain a constant AC current amplitude, forming an effective current source. Induced voltage between electrodes 112 and 113 may serve as a measure of the impedance, and variations in the induced voltage may reflect impedance variations.

Bioimpedance signals may be indicative, for example, of hemodynamic conditions within a first and/or a second hemisphere of a subject's brain. First and second hemispheres may refer to right and left hemispheres of a subject's brain, in any order. A signal indicative of hemodynamic conditions within a particular side of a subject's brain may be obtained from the same side of the subject's head, via electrodes or the like, or may be obtained from an opposite side of the subject's head. Hemodynamic conditions may include, for example, cerebral blood volume, cerebral blood flow, cerebral perfusion pressure, intracranial pressure, and any other parameter that may be at least partially reflective of cerebral conditions. A bioimpedance signal indicative of hemodynamic conditions within a particular side of a subject's brain may also be obtained from other locations, such as on the neck of a subject, where, for example, carotid arteries are located.

A bioimpedance signal may also be measured from output current at more than a single AC frequency. The output current may include a set of predefined frequencies and amplitudes, with detection of the measured voltage at all the frequencies or a part of the frequency range. Bioimpedance signals may be obtained in response to current at a single AC frequency or at multiple frequencies. Multiple frequencies may be a set of discrete predefined frequencies or continuous frequency sweep, such as chirped frequency. Multiple frequencies may also combine to form predefined waveforms such as triangular or square waves.

At least one processor 160, illustrated in FIG. 1, configured to measure, monitor, and/or analyze bioimpedance signals may be included in Cerebral Perfusion Monitor 130, as part of exemplary headset apparatus 100. Processor 160 may be configured to perform all or some of the signal analysis methods described herein, or some of those functions might be performed by a separate processor. Processor 160 may also be configured to perform any common signal processing task known to those of skill in the art, such as filtering, noise-removal, etc. Processor 160 may further be configured to perform pre-processing tasks specific to the signal analysis techniques described herein. Such pre-processing tasks may include, but are not limited to, removal of signal artifacts, such as motion and respiratory artifacts.

Exemplary retainer 180 may include further devices or elements, such as an additional sensor or sensors 140, for augmenting bioimpedance measurements or for performing measurements in addition to bioimpedance measurements. In one embodiment, additional sensor 140 may include, for example, a light emitting diode 141 and a photo detector 142 for performing Photo Plethysmography (PPG) measurements either in conjunction with or in alternative to bioimpedance signal measurements. The exemplary retainer 180 may further include various circuitry 170 for signal processing or other applications and may include the capability to transmit data wirelessly to cerebral perfusion monitor 130 or to other locations. In an additional embodiment, cerebral perfusion monitor 130 may be integrated with retainer 180. Although illustrated in the example of FIG. 1, additional sensor 140 and circuitry 170 may be omitted.

As mentioned previously, exemplary retainer 180 may include one or more additional sensors 140 in addition to or as an alternative to electrical or electrode including devices for measuring bioimpedance. For example, additional sensor 140 may include one or more components configured to obtain PPG data from an area of the patient. Additional sensors 140 may comprise any other suitable devices, and are not limited to the single sensor illustrated in FIG. 1. Other examples of additional sensor 140 include devices for measuring local temperature (e.g., thermocouples, thermometers, etc.) and/or devices for performing other biomeasurements.

Exemplary retainer 180 may include any suitable form of communicative mechanism or apparatus. For example, retainer 180 may be configured to communicate or receive data, instructions, signals or other information wirelessly to another device, analytical apparatus and/or computer. Suitable wireless communication methods may include radiofrequency, microwave, and optical communication, and may include standard protocols such as Bluetooth, WiFi, etc. In addition to, or in alternative to these configurations, exemplary retainer 180 may further include wires, connectors or other conduits configured to communicate or receive data, instructions, signals or other information to another device, analytical apparatus and/or computer. Exemplary retainer 180 may further include any suitable type of connector or connective capability. Such suitable types of connectors or connective capabilities may include any standard computer connection (e.g., universal serial bus connection, firewire connection, Ethernet or any other connection that permits data transmission). Other suitable types of connectors or connective capabilities may further or alternatively include specialized ports or connectors configured for the exemplary apparatus 100 or configured for other devices and applications.

Blood flow into and out of the head, and more specifically, the brain, during a cardiac cycle may result in a cyclic change of the bioimpedance signal measured by electrodes 110. Bioimpedance changes may correlate with blood content in the head and brain. In general, because blood has a relatively low impedance when compared with tissue found in the head, higher blood content results in lower impedance. Blood flow into brain tissue may also vary the frequency response of the brain impedance. Comparing bioimpedance measurements at different frequencies may provide additional information indicative of hemodynamic conditions.

Figure 2:
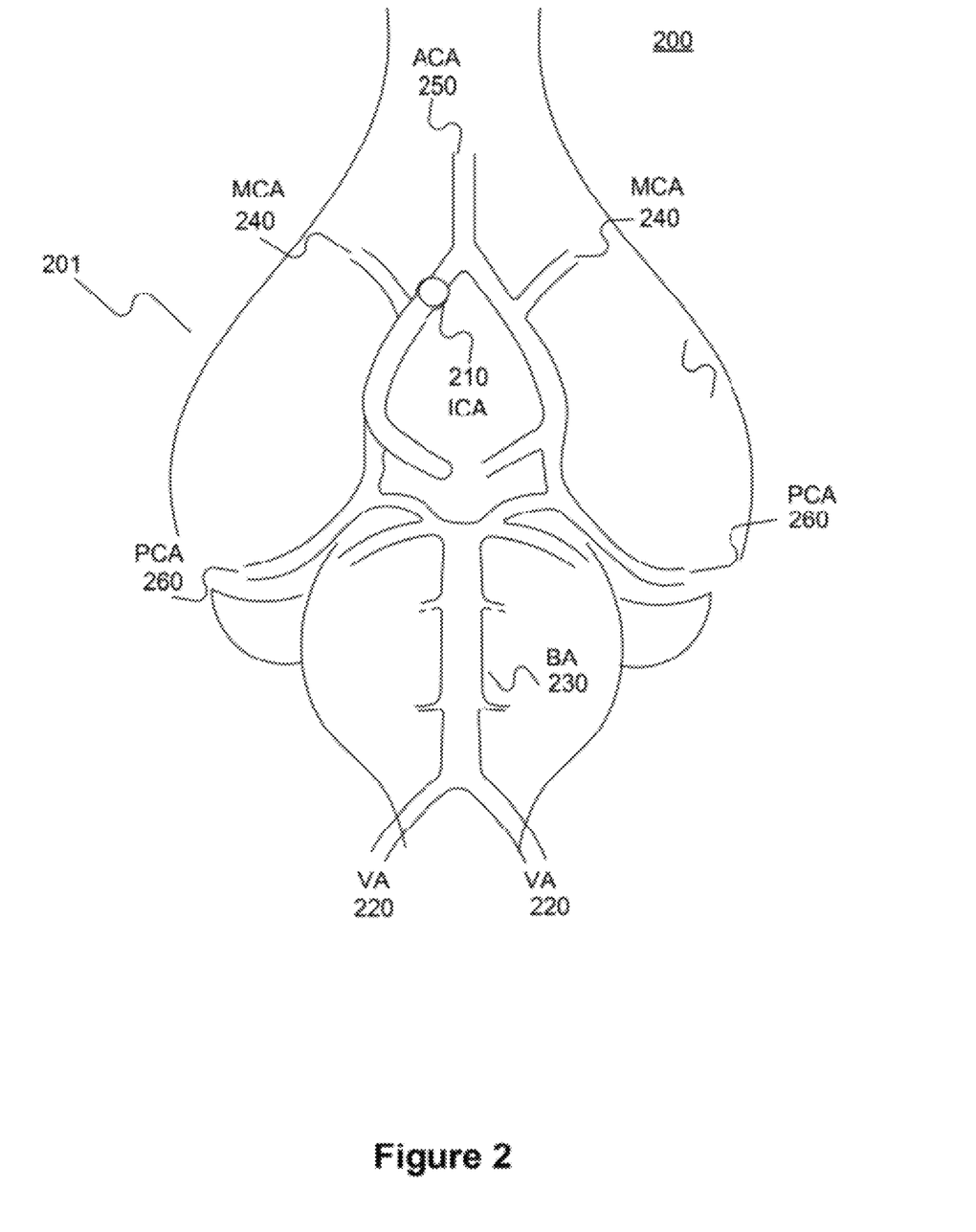
FIG. 2 provides a diagrammatic representation of major cerebral arteries.

FIG. 2 provides a diagrammatic representation of major features of the cerebral vasculature 200. The cerebral vasculature in FIG. 2 is viewed from below the brain, with the top of the page representing the front of a subject. The blood supply to the brain 201 comes from four main arteries traversing the neck. The larger two are the right and left internal carotid arteries (ICA) 210, in the front part of the neck. The vertebral arteries (VA) 220 are located in the back of the neck and join to form the basilar artery (BA) 230. The internal carotid arteries and the basilar arteries are connected by Posterior Communicating Artery (not shown) and Anterior Communicating Artery (not shown) to form the Circle of Willis (COW). In an ideal patient, the COW is a network of connected arteries that allows blood supply to the brain 201 even when one or more of the feeding arteries is blocked.

The main arteries that supply blood to the brain 201 are the Middle Cerebral Arteries (MCAs) 240, Anterior Cerebral Arteries (ACAs) 250, and Posterior Cerebral Arteries (PCAs) 260. The MCAs 240 may be one area of interest when diagnosing decreased blood flow to portions of the brain 201. The MCAs 240 are the sole blood supply to the largest brain region—about two thirds of each brain hemisphere.

Ischemic Stroke may occur when the blood supply to the brain is interrupted by occlusion of one of the supplying arteries. In most acute stroke cases, the cause of the occlusion is emboli that developed near the heart and drifted with the blood flow towards the brain. Large strokes are often associated with diminished blood supply to the MCA territory, either by partial or full blockage of an ICA 210, or by occlusion of all or part of the MCA 240. Because the MCA territory, i.e. the brain region that receives a majority of its blood supply from the MCA, represents a large area, such an occlusion may affect a large part of the brain. Thus, monitoring blood flow in the MCA 240 territory, and providing an prediction of hemodynamic conditions in this region may be useful.

As will be explained in greater detail below, the electrodes connected to exemplary retainer 180 may be placed such that signal pathways coincide, cross, or interact to some extent with the MCAs 240 or other arteries. For example, electrodes 110 may be positioned to straddle the MCA 240, such that the MCA 240 runs between a pair of planes dissecting the head and extending through each electrode. Thus, measures of signal properties such as impedance may be indicative of and/or related to blood flow in an MCA 240 or other arteries. Specific electrode 110 placement in and around the patient's temples, facilitated by specific configurations of retainer 180, for example, may enable generation of signals including information relating to blood flow in the MCA 240, in particular.

Figure 3:
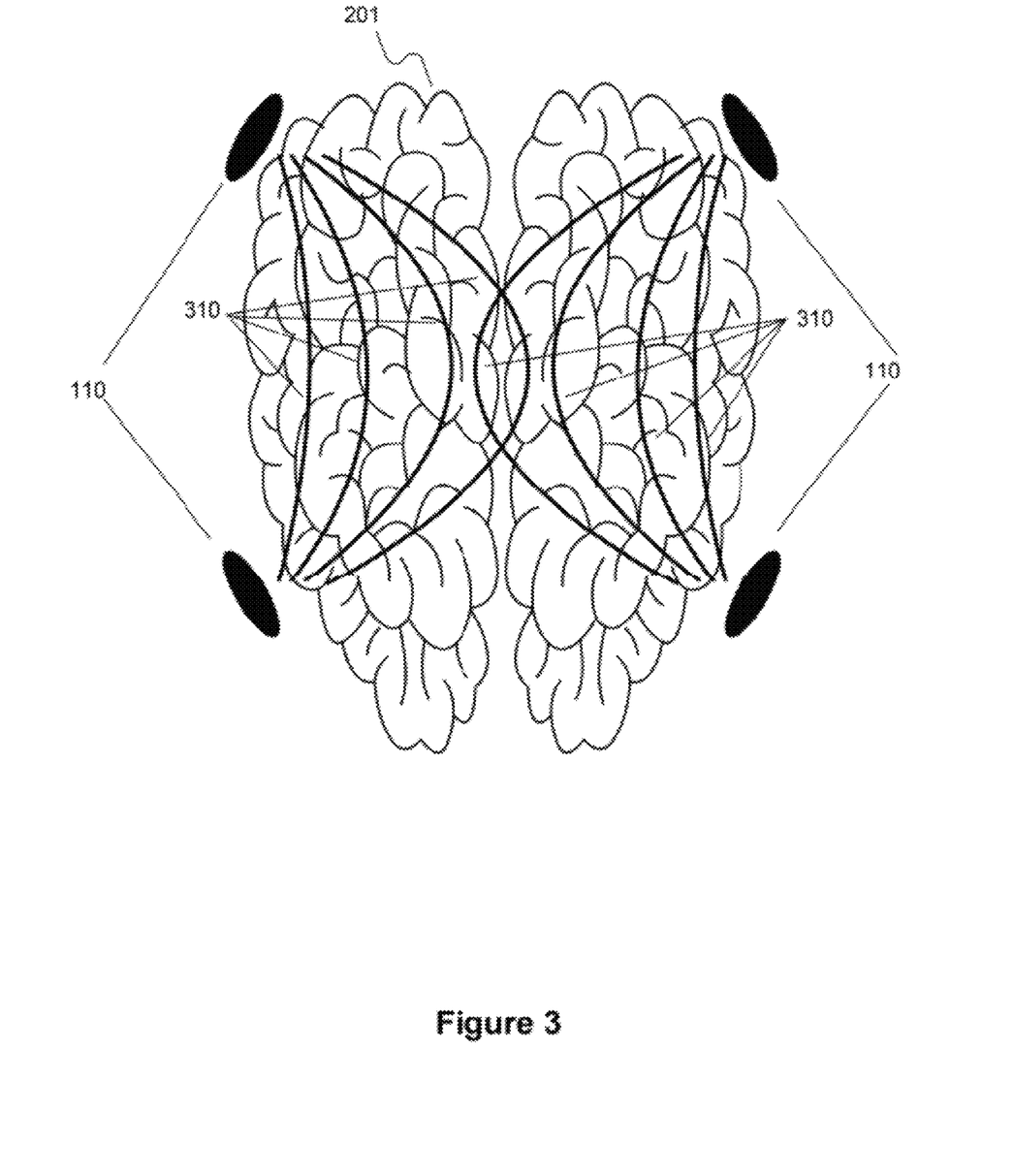
FIG. 3 provides a diagrammatic representation of exemplary bioimpedance signal pathways in the brain of a subject consistent with exemplary embodiments of the invention.

FIG. 3 provides a diagrammatic representation of exemplary bioimpedance signal pathways 310 in the brain 201 of a subject. The exemplary configuration illustrates multiple signal pathways 310 through each of the right and left brain hemispheres. The multiple signal pathways extend between electrodes 110 affixed to the head of a subject via retainer 180. The impedance of the signal pathways 310 may be influenced by the presence or absence of blood along the pathway, because blood has a relatively low impedance. Further, the shape and direction of signal pathways 310 may be influenced by the impedance of the signal pathways 310. At least some of the signal pathways 310 may be coincident with brain vasculature. Signal properties may thus be measured that are indicative of hemodynamic conditions, such as blood volume, in the blood vessels of the brain 201. Changes in bioimpedance may thus be indicative of changes in blood flow in the brain 201. Signal pathways 310 depicted in FIG. 3 are representative of only a small number of an infinite number of pathways which may exist in the general area of signal pathways 310.

Figure 4:
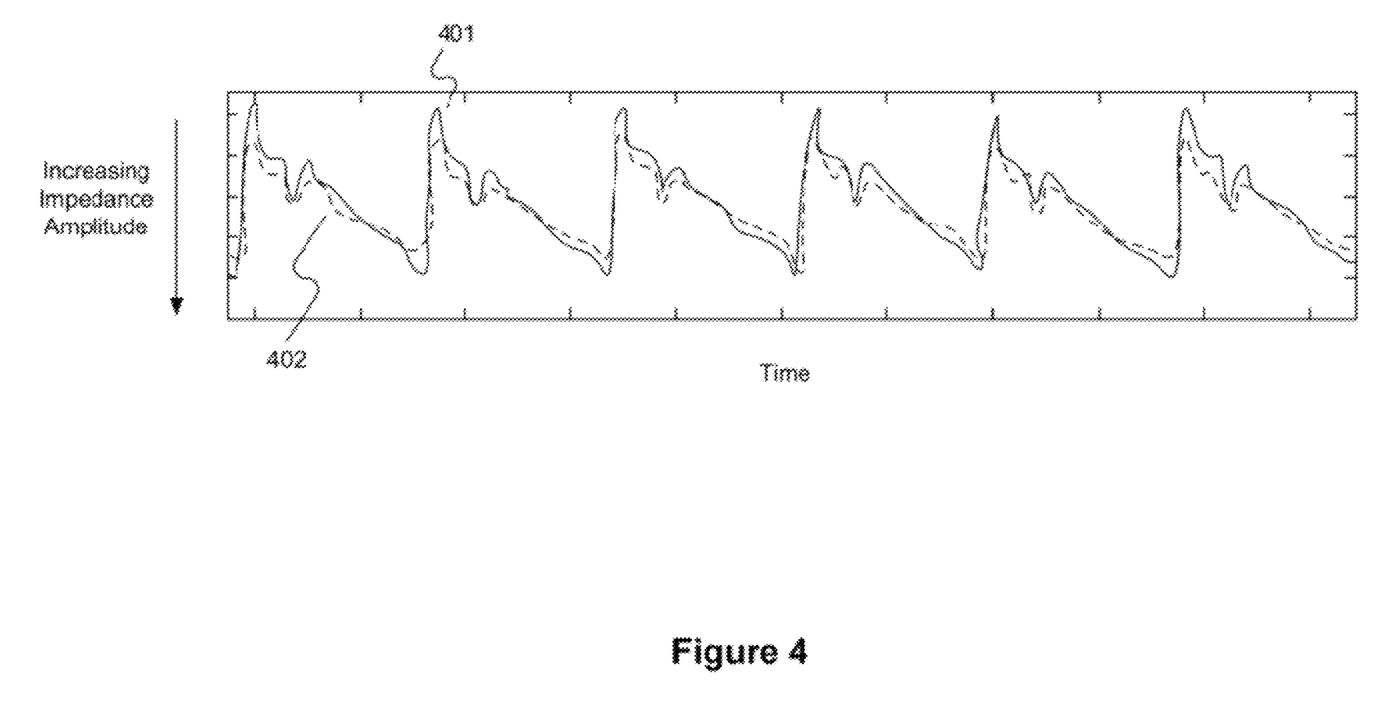
FIG. 4 provides a diagrammatic representation of an exemplary bioimpedance signal obtained from a cerebro-hemodynamic measurement apparatus consistent with exemplary embodiments of the invention, FIG. 5 provides a diagrammatic representation of an exemplary sensitivity map of a brain.

FIG. 4 provides a diagrammatic representation of exemplary bioimpedance signals 401, 402 obtained by an exemplary headset apparatus 100. The illustrated bioimpedance signals 401, 402 show a periodic change of impedance amplitude for right and left brain hemispheres, respectively, of a relatively healthy patient, obtained using an exemplary headset apparatus 100. Thus, signals 401 and 402 are examples of first and second signals associated with a brain of a subject, and which each are indicative of a hemodynamic characteristic of the subject's brain.

As shown in FIG. 4, bioimpedance amplitude exhibits a periodic cycle for both left and right brain hemispheres. The period of this change in amplitude is approximately the period of a cardiac cycle. In FIG. 4, the y-scale is inversely correlated with impedance amplitude. That is, high values of impedance amplitude are reflected by low values in the signal as illustrated in FIG. 4. More specifically, each cardiac cycle actually begins with a decrease in impedance that corresponds to a rapid increase in blood flow, reflected in the signal peaks illustrated in FIG. 4. The maxima shown (i.e., the signal peaks) in each periodic cycle in FIG. 4 are indicative of impedance minima that correspond to a maximal blood flow in response to a heartbeat.

According to some embodiments of the present disclosure, a retainer may position a first electrode and a second electrode based on a sensitivity map. A sensitivity map, as used herein, represents the sensitivity of measured signals to physiological changes in different areas of the head. For instance, measured bioimpedance signals of the head may be affected by changes in the impedance of the head. The sensitivity of the measured signals to the changes in impedance in different areas of the head may be charted on a sensitivity map. Such a sensitivity map may be representative of the infinite number of signal pathways 310. Further, a sensitivity map measured by electrodes may be affected by the placement of the electrodes. Sensitivity maps may be two dimensional, representing sensitivities across a cross section of the head, and may be three dimensional, representing sensitivities throughout the brain.

Figure 5:
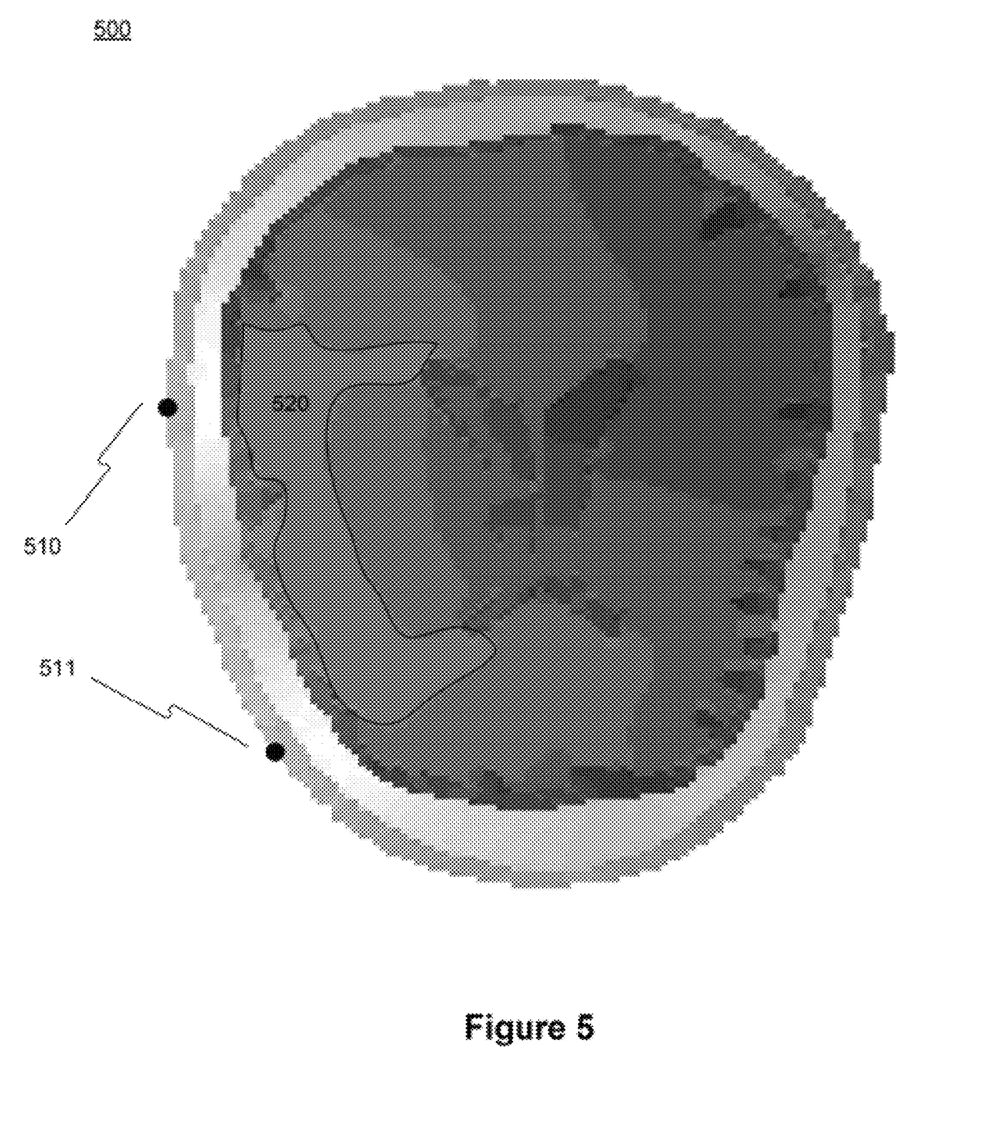

An exemplary two dimensional impedance sensitivity map may be explained with reference to FIG. 5. Sensitivity map 500, as illustrated in FIG. 5, represents the relative change of measured voltage to changes in the impedance of different regions of the brain. In FIG. 5 the sensitivity of the different areas of the head is represented by the shading from white to black. Lighter shades represent areas of higher sensitivity. The black outline of around region 520 serves to highlight this region, discussed in greater detail below, and does not represent sensitivity values in the impedance sensitivity map. As discussed above, impedance in the brain may change according to blood flow characteristics. Measuring impedance in the brain may be performed by driving a current between electrodes affixed to the head and measuring the resultant voltage. The resulting voltage changes according to changes in impedance in the head. When impedance changes in a relatively high sensitivity area of the brain, the resulting voltage change may be relatively high. When impedance changes in a relatively low sensitivity area of the brain, the resulting voltage changes may be relatively low. Thus, a sensitivity map may illustrate the areas of the brain in which, according to a certain placement of electrodes, impedance changes have the greatest effect on signal measurements.

Figure 6:
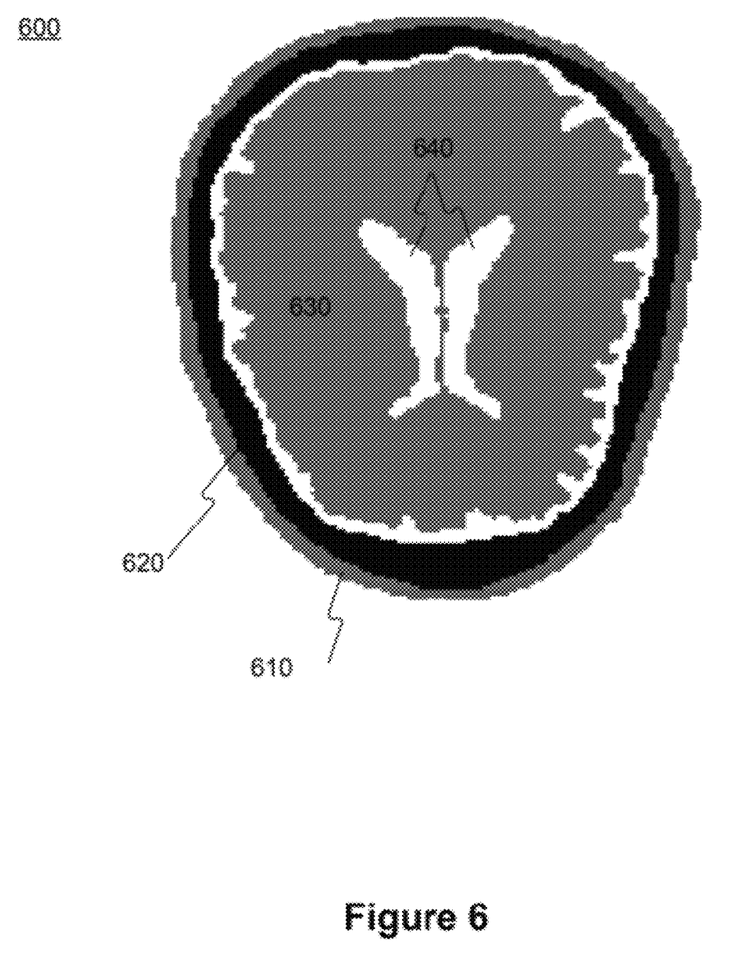
FIG. 6 provides a diagrammatic representation of an exemplary conductance model of a brain.

Sensitivity maps, such as that shown in FIG. 5, may be generated through computer simulation methods utilizing a conductance model of the brain. FIG. 6 illustrates a conductance cross section 600 of the brain. The image shown in FIG. 6 was obtained from a CT scan, and is divided into separate conductivity regions. External scalp region 610 and gray and white matter region 630, both shown in gray, have a conductivity of approximately 0.33 Siemens/meter (S/m). Skull region 620, shown in black, has a conductivity of approximately 0.0042 S/m. Finally, internal ventricles 640, containing cerebral spinal fluid shown in white, have a conductivity of approximately 2 S/m. Cerebral spinal fluid also fills the area between the skull region 620 and the gray and white matter region 630, as illustrated by the white layer between the two. Also illustrated is a schematic MCA Territory 650, extending from the posterior and anterior horns of the lateral cerebral ventricle to the skull. While FIG. 6 illustrates a conductance model of the brain, an impedance model may also be used in computer simulation methods to generate an impedance sensitivity map, such as that shown in FIG. 5. Because conductance is the inverse of impedance, either measurement may be used to generate an impedance sensitivity map.

Utilizing a conductance model such as that illustrated in FIG. 6, sensitivity maps of the head for various electrode positions may be computed using computer simulation methods. Computer simulation methods may be used to solve the equations that govern current flow through the brain, using a conductance model and electrode positions as input parameters. Computer simulations may thus generate sensitivity maps showing the relative change of measured voltage to changes in conductance in different areas of the brain.

Returning now to FIG. 5, the use of an impedance sensitivity map in determining electrode position may be described. In the impedance sensitivity map illustrated in FIG. 5, generated using electrode positions 510, 511 as input parameters, MCA impedance region 520 covers much of the area associated with the right MCA territory 650, to a depth of a few centimeters in the brain. MCA impedance region 520 extends to the two "horns" 512 and 514 of the right ventricles, showing a preference to expand inwards when the electrodes are positioned opposite appropriate ventricle extensions. Electrode 510 may be positioned posterior to the MCA, generally opposing the posterior horn 514 of the right lateral ventricle. Electrode 511 may be positioned anterior to the MCA, generally opposing the anterior horn 512 of the right lateral ventricle.

The sensitivity in MCA impedance region 520, as illustrated in FIG. 5, is approximately twice as high as that of the surrounding areas of darker gray. The relatively high sensitivity shown for the skull does not contribute to changes in a measured bioimpedance signal, because there is no pulsatile blood flow in the skull. Electrode positioning, as shown in FIG. 5, that increases the sensitivity of signal measurements to impedance changes in the MCA territory 650 may be useful because large strokes are often associated with diminished blood supply to the MCA territory 650. Electrode positioning that increases the sensitivity of bioimpedance signal measurements to impedance changes in the MCA territory 650 may also increase the sensitivity of bioimpedance signal measurements to blood flow changes in the MCA territory 650. In accordance with some embodiments of the present disclosure, first and second electrodes, connected by an electrical conductor, may be positioned such that, when they are connected to a circuit through which current flows, the electrodes enable current to flow from one electrode on one side of the MCA through the lateral cerebral ventricle and to the other electrode on a second side of the MCA, opposite the first side.

On the head, electrode position 511 corresponds to a location at the edge of the forehead and electrode position 510 corresponds to a location above the ear, near the widest area of the head. Exemplary retainer 180 may be configured to maintain electrode positions according to the sensitivity map 500. Depending on the head size of a subject, the spacing of electrode positions 510 and 511 to achieve the illustrated coverage of the MCA territory 650 may vary. For an average head size, this spacing may be 85 mm. According to some embodiments of the present disclosure, exemplary retainer 180 may maintain a spacing between electrode positions 510 and 511 of between 70 mm and 100 mm, and between 75 mm and 95 mm. According to other embodiments of the present disclosure, a first electrode may be connected to the retainer at a first position such that when the retainer is oriented on a head of a subject, the first electrode is located anterior to an MCA of the subject and generally opposed to an anterior horn of a lateral cerebral ventricle, and a second electrode may be connected to the retainer at a second position, such that when the retainer is oriented on the head of the subject, the second electrode is located posterior to the MCA and generally opposed to a posterior horn of the lateral cerebral ventricle.

Embodiments have thus far been described with respect to the MCA territory 650 in one hemisphere of the brain. According to additional embodiments, third and fourth electrodes may be connected to a retainer at third and fourth positions, such that when the retainer is oriented on the head of the subject, the third electrode is located on a side of the head opposite to the first electrode, and the fourth electrode is located on a side of the head opposite the second electrode, and wherein the third and fourth electrodes are paired such that current associated with the first and second electrodes is enabled to flow through a first lateral cerebral ventricle, and current associated with the third and fourth electrodes is enabled to flow through a second lateral cerebral ventricle, opposite the first lateral cerebral ventricle. In this fashion, third and fourth electrodes may be enabled to perform similar measurements as performed by a first and second electrode, but on the opposite side of a subject's head. Any of the structures and functions described herein as pertaining to one side of a subject's head may also be applied, simultaneously or at different times, to the opposite side of a subject's head.

Figure 7:
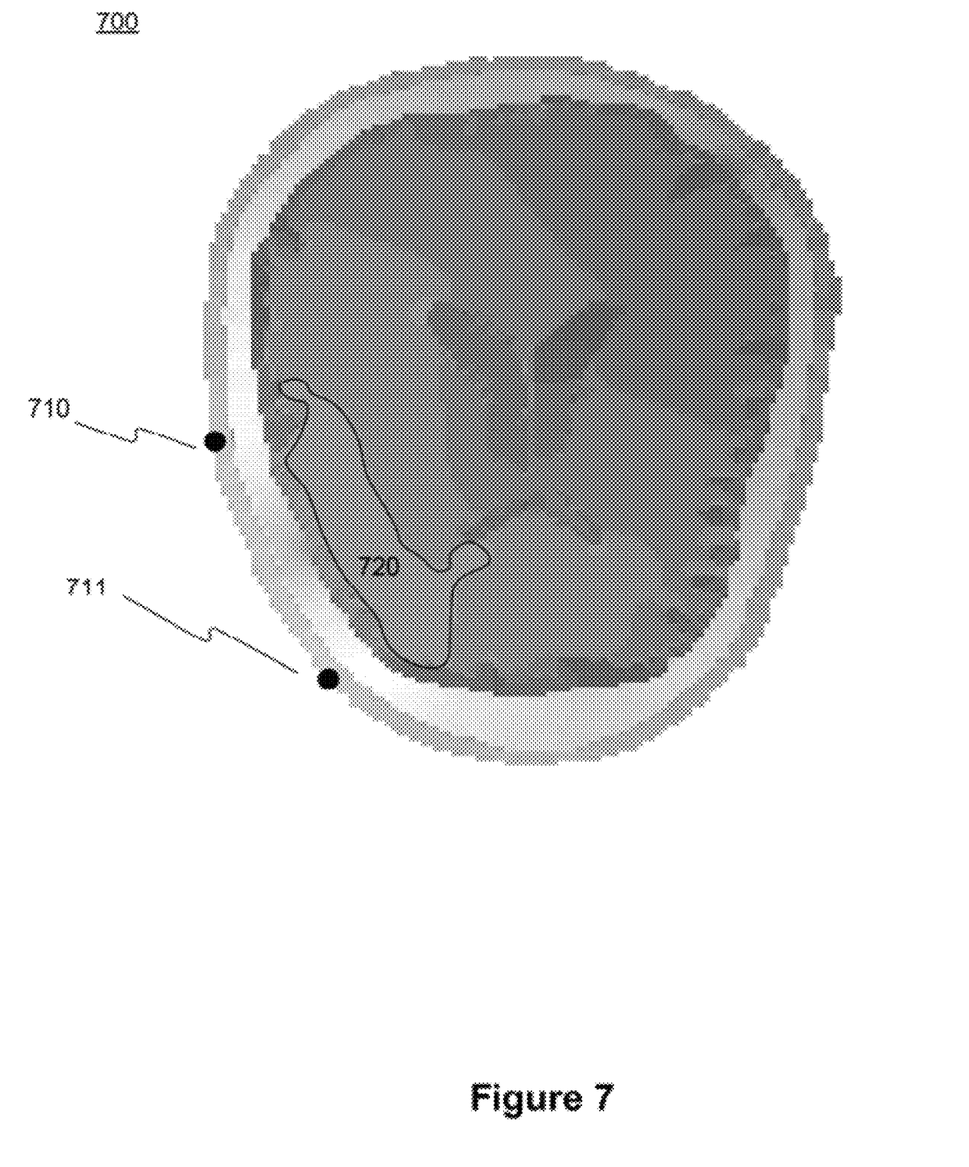
FIG. 7 provides a diagrammatic representation of another exemplary sensitivity map of a brain.

Sensitivity map 500 illustrates an exemplary impedance sensitivity map for achieving increased measurement sensitivity to changes in blood flow in the MCA territory 650. Other embodiments, however, may involve the positioning of electrodes according to different sensitivity maps, for increasing measurement sensitivity to changes in blood flow in other brain regions. FIG. 7 illustrates a sensitivity map 700 displaying a maximum impedance sensitivity region 720 that does not correspond as well as sensitivity map 500 to the MCA territory 650. Sensitivity map 700, generated based on electrode positions 710 and 711, may thus demonstrate less sensitivity to blood flow variations in the MCA territory 650. This may be beneficial, if it is desired to obtain bioimpedance measurements that are more indicative of blood flow in other regions of the brain than the MCA territory 650.

Consistent with the present disclosure, at least one processor may be configured to output information for predicting a hemodynamic condition associated with an MCA territory 650 on a side of the head of the subject on which the first and second electrode are positioned based on the at least one bioimpedance signal. As used, herein, "information for predicting a hemodynamic condition associated with an MCA territory," may include any type of information that may aid a physician in detecting, diagnosing, understanding, or predicting a hemodynamic condition associated with an MCA territory 650. Such information may, for example, include a direct indication of a hemodynamic condition, or include information that assists in diagnosis or prediction of a hemodynamic condition. Information for predicting a hemodynamic condition may include specific information about the location and extent of the condition, or may include general information indicative of a change in condition. A hemodynamic condition associated with an MCA territory 650 may mean any hemodynamic condition occurring within an MCA territory 650, as well as hemodynamic conditions occurring outside of an MCA territory 650 due to conditions within an MCA territory 650.

The output information may be as simple as an indicator to a medical professional that a significant hemodynamic condition exists. Alternatively, or additionally, it may include informational output characterizing, for example, one or more of a magnitude of a bioimpedance signal, a change in magnitude of a bioimpedance signal over time, and any other data that might indicate a hemodynamic condition, an extent of a hemodynamic condition, or a change in extent of a hemodynamic condition.

Figure 8:
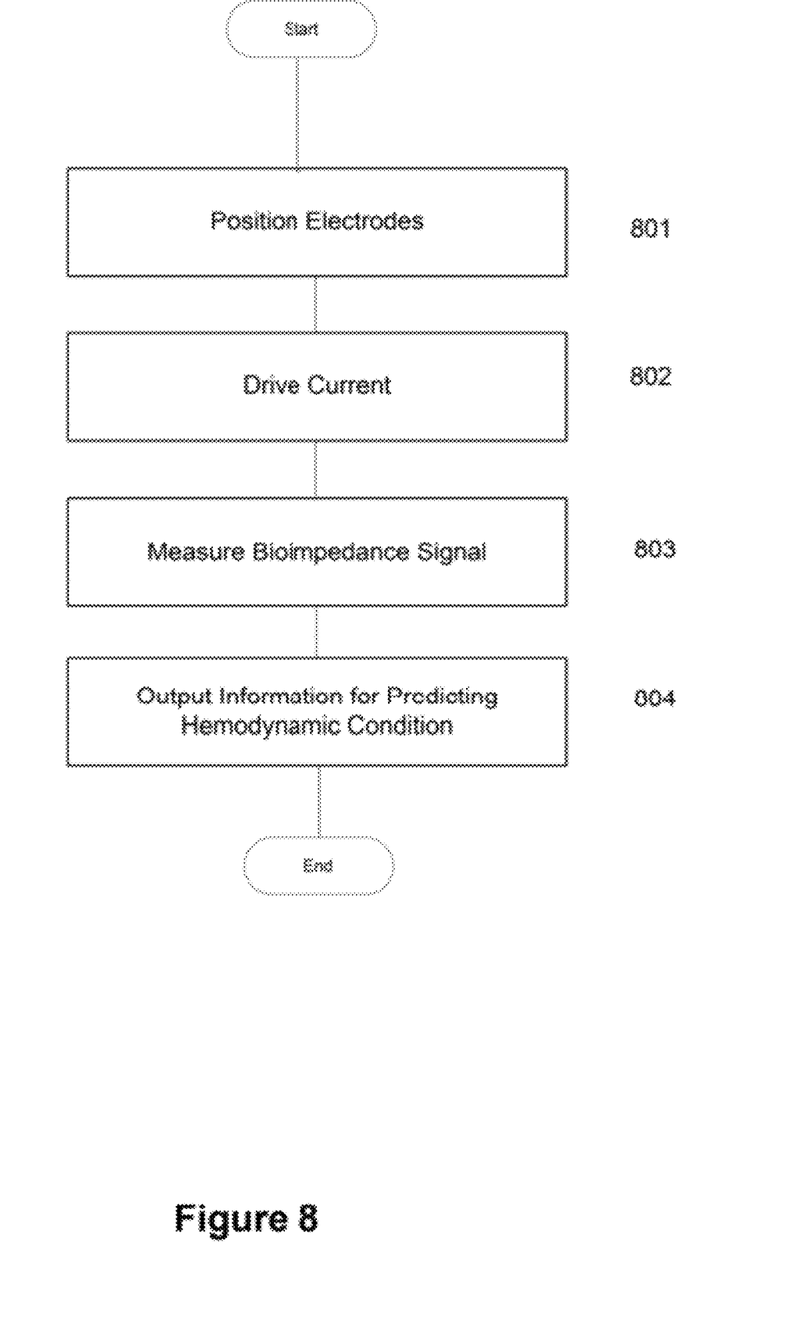
FIG. 8 is a flowchart showing the steps of an exemplary method for predicting a hemodynamic condition associated with an MCA territory.

In an embodiment consistent with the present disclosure, a method for predicting a hemodynamic condition associated with an MCA territory 650 may be provided. FIG. 8 is a flowchart showing the steps of an exemplary method for predicting a hemodynamic condition associated with an MCA territory 650. At step 801, first and second electrodes may be positioned on the head of a subject. The electrodes may be positioned such that the first electrode is located anterior to an MCA of the subject and generally opposes an anterior horn of a lateral cerebral ventricle and the second electrode is located posterior to the MCA and generally opposes a posterior horn of the lateral cerebral ventricle. The electrodes may be positioned through the use of a structural device, such as exemplary retainer 180, or any other suitable mechanism for positioning the electrodes on the head of a subject, such as adhesive.

At step 802, current may be driven between the first and second electrodes. The current may be generated, for instance, by cerebral perfusion monitor 130, or any other suitable current generator, and conducted via electrical conductor 190 to and from the first and second electrodes. The driven current may include an AC signal of constant amplitude and stable frequency, and/or may include signals of varying amplitude and frequency.

At step 803, a bioimpedance signal resulting from driving the current may be measured, according to methods and devices previously described. For example, the current may be measured via voltage electrodes 110 by a processor 160 included in cerebral perfusion monitor 130.

At step 804, information may be output for predicting a hemodynamic condition associated with the MCA territory 650 on a side of the head on which the first and second electrodes are positioned, based on the measured bioimpedance signal. The information may be outputted, for example, by processor 160.

Disclosure of uses of embodiments of the invention for detection, diagnosis, and monitoring of strokes and occlusions is exemplary only. In its broadest sense, the invention may be used in connection with the detection, diagnosis, and/or treatment of any hemodynamic brain condition detectable using the principles described herein. Further, it should be appreciated that the methods and apparatus described herein to predict hemodynamic brain conditions in an MCA territory 650 of a subject may be generalized to predict hemodynamic brain conditions of any genesis, including stroke, vascular degeneration, etc., in any regions of a subject's brain. Alternative embodiments will become apparent to those skilled in the art to which the present invention pertains without departing from its spirit and scope. Accordingly, the scope of the present invention is defined by the appended claims rather than the foregoing description.

What is claimed is:

1. A headset apparatus, comprising:
a retainer;
a first electrode configured to connect to the retainer at a first position;
a second electrode configured to connect to the retainer at a second position;
the retainer comprising a substantially inflexible portion shaped to fit a temporal region of a head of a subject, the temporal region being adjacent to an ear of the subject, the portion being shaped to maintain, when the retainer is oriented on the head of the subject:

a position of the first electrode anterior to a middle cerebral artery (MCA) of the subject and opposing an anterior horn of a lateral cerebral ventricle, and a position of the second electrode posterior to the MCA, above the ear of the subject, and opposing a posterior horn of the lateral cerebral ventricle; and at least one electrical conductor enabling the first electrode and the second electrode to be connected in a circuit, such that when the first electrode is in the first position and the second electrode is in the second position and the first and second electrodes are connected to a circuit through which current flows, the retainer, the first electrode, and the second electrode cooperate to enable current to flow from one of the first and second electrodes on a first side of the MCA through the lateral cerebral ventricle and to another of the first and second electrodes on a second side of the MCA, opposite the first side, wherein the retainer is adapted to maintain relative positions of the first electrode and the second electrode with respect to one another.

2. The headset apparatus of claim 1, wherein the portion maintains a spacing of between 70 mm and 100 mm between the first electrode and the second electrode.

3. The headset apparatus of claim 1, wherein the portion maintains a spacing of between 75 and 95 mm between the first electrode and the second electrode.

4. The headset apparatus of claim 1, wherein the portion positions the first and second electrodes according to a sensitivity map.

5. The headset apparatus of claim 1, wherein the portion positions the first electrode to be glued to exposed skin on a forehead of the subject and positions the second electrode to be glued to exposed skin above the ear of the subject.

6. The headset apparatus of claim 1, wherein the portion positions the first and second electrodes such that the first and second electrodes are not directly above external blood vessels or muscled areas.

7. The headset apparatus of claim 1, wherein the electrodes are oriented to enable current to pass from the first electrode, through the lateral cerebral ventricle and to the second electrode.

8. The headset apparatus of claim 1, further comprising a third electrode connected to the retainer at a third position and a fourth electrode connected to the retainer at a fourth position, such that when the retainer is oriented on the head of the subject, the third electrode is located on a side of the head opposite to the first electrode, and the fourth electrode located on a side of the head opposite the second electrode, and wherein the third and fourth electrodes are paired such that current associated with the first and second electrodes is enabled to flow through a first lateral cerebral ventricle, and current associated with the third and fourth electrodes is enabled to flow through a second lateral cerebral ventricle, opposite the first lateral cerebral ventricle.

9. The headset apparatus of claim 1, further comprising at least one processor configured to measure at least one bioimpedance signal from the current that flows from one of the first and second electrodes to another of the first and second electrodes.

10. The headset apparatus of claim 9, wherein the at least one processor is further configured to output information for predicting a hemodynamic condition associated with an MCA territory on a side of the head of the subject on which the first and second electrode are positioned based on the at least one bioimpedance signal.

11. The headset apparatus of claim 8, further comprising at least one processor configured to measure at least one bioimpedance signal from the current associated with the first and second electrodes and at least one other bioimpedance signal from the current associated with the third and fourth electrodes.

12. The headset apparatus of claim 11, wherein the at least one processor is further configured to output information for predicting a hemodynamic condition of an MCA territory associated with a side of the head of the subject on which the first and second electrodes are positioned based on the at least one bioimpedance signal, and for predicting a hemodynamic condition associated with an MCA territory on a side of the head of the subject on which the third and fourth electrode are positioned based on the at least one other bioimpedance signal.

13. The headset apparatus of claim 1, wherein the first and second electrodes are configured to drive current therebetween and to enable measurement of a resulting voltage.

14. The headset apparatus of claim 1, wherein the first electrode is a first current electrode and the second electrode is a second current electrode, and wherein the headset apparatus further includes a first voltage electrode and a second voltage electrode, wherein the first and second voltage electrodes are respectively located on the retainer at positions adjacent to the first and second current electrodes.

15. A method for predicting a hemodynamic condition associated with a middle cerebral artery (MCA) an MCA territory, the method comprising: orienting a retainer on the head of the subject, the retainer comprising a substantially inflexible portion shaped to fit a temporal region of a head of a subject, the temporal region being adjacent to an ear of the subject, the portion shaped to maintain: positioning a first electrode connected to the retainer at a first position on a head of a subject, such that the first electrode is located anterior to an MCA of the subject and generally opposes opposing an anterior horn of a lateral cerebral ventricle, positioning a second electrode connected to the retainer at a second position on the head of the subject, such that the second electrode is located posterior to the MCA, above the ear of the subject, and generally opposes opposing a posterior horn of the lateral cerebral ventricle, and wherein the retainer is adapted to maintain relative positions of the first electrode and the second electrode with respect to one another; driving a current between the first electrode and the second electrode from one of the first and second electrodes on a first side of the MCA through the lateral cerebral ventricle and to another of the first and second electrodes on a second side of the MCA, opposite the first side; measuring a bioimpedance signal that results from driving the current; and outputting information for predicting a hemodynamic condition associated with the MCA territory on a side of the head on which the first and second electrodes are positioned, based on the bioimpedance signal.

16. The method of claim 15, wherein during driving, the retainer maintains a spacing of between 70 mm and 100 mm between the first electrode and the second electrode.

17. The method of claim 15, wherein during driving, the retainer maintains a spacing of between 70 and 95 mm between the first electrode and the second electrode.

18. The method of claim 15, wherein, during driving, the retainer maintains positioning of the first and second electrodes according to a sensitivity map.

19. The method of claim 15, wherein, positioning the first electrode further comprises gluing the first electrode to exposed skin on the forehead and positioning the second electrode further comprises gluing the second electrode to exposed skin above the ear.

20. The method of claim 15, wherein the first and second positions are not directly above external blood vessels or muscled areas.

21. The method of claim 15, wherein, during driving, the relative positions of the first electrode and the second electrode with respect to one another cause further comprising orienting the first and second electrodes to cause current to concentrate in a generally wedge-shaped region having a wedge apex generally intersecting the anterior horn of the lateral cerebral ventricle and a wedge base generally oriented toward the subject's skull.

22. The method of claim 15, further comprising positioning a third electrode at a third position on the head of the subject, such that the third electrode is located on a side of the head opposite the first electrode, positioning a fourth electrode at a fourth position on the head of the subject, such that the fourth electrode is located on the side of the head opposite the second electrode; driving a second current between the third electrode and the fourth electrode; measuring a second bioimpedance signal that results from driving the second current; and outputting information for predicting a hemodynamic condition associated with an MCA territory on a side of the head on which the third and fourth electrodes are positioned, based on the second bioimpedance signal.

\* \* \* \* \*